US006775575B2

(12) United States Patent
Bommannan et al.

(10) Patent No.: US 6,775,575 B2
(45) Date of Patent: Aug. 10, 2004

(54) SYSTEM AND METHOD FOR REDUCING POST-SURGICAL COMPLICATIONS

(76) Inventors: D. Bommi Bommannan, 1977 Wimbledon Pl., Los Altos, CA (US) 94024; Michael D. Laufer, 1259 El Camino Real, #211, Menlo Park, CA (US) 94025

( * ) Notice: Subject to any disclaimer, the term of this patent is extended or adjusted under 35 U.S.C. 154(b) by 0 days.

(21) Appl. No.: 10/085,237

(22) Filed: Feb. 26, 2002

(65) Prior Publication Data

US 2002/0183734 A1 Dec. 5, 2002

Related U.S. Application Data

(60) Provisional application No. 60/271,475, filed on Feb. 26, 2001.

(51) Int. Cl.[7] .............................. A61F 2/00; A61B 18/18
(52) U.S. Cl. ....................... 607/101; 607/102; 607/113; 606/51; 606/52
(58) Field of Search .............................. 606/42, 41, 45, 606/48–52; 607/96, 98, 99, 101, 102, 113

(56) References Cited

U.S. PATENT DOCUMENTS

| 3,527,224 A | 9/1970 | Rabinowitz |
| 3,591,676 A | 7/1971 | Hawkins et al. |
| 3,667,472 A | 6/1972 | Halpern |
| 3,995,641 A | 12/1976 | Kronenthal et al. |
| 4,035,334 A | 7/1977 | Davydov et al. |
| 4,650,826 A | 3/1987 | Waniczek et al. |
| 5,213,580 A | 5/1993 | Slepian et al. |
| 5,328,687 A | 7/1994 | Leung et al. |
| 5,344,420 A | 9/1994 | Hilal et al. |
| 5,417,687 A | 5/1995 | Nardella et al. |
| 5,428,699 A | 6/1995 | Pon |
| 5,456,684 A | * 10/1995 | Schmidt et al. ............... 606/41 |
| 5,540,684 A | 7/1996 | Hassler, Jr. |
| 5,599,347 A | 2/1997 | Hart et al. |
| 5,690,675 A | 11/1997 | Sawyer et al. |
| 5,702,390 A | 12/1997 | Austin et al. |
| 5,711,958 A | 1/1998 | Cohn et al. |
| 5,728,143 A | 3/1998 | Gough et al. |
| 5,779,699 A | 7/1998 | Lipson |
| 5,782,900 A | 7/1998 | de la Rama et al. |
| 5,791,352 A | 8/1998 | Reich et al. |
| 5,846,235 A | 12/1998 | Pasricha et al. |
| 5,906,609 A | 5/1999 | Assa et al. |

(List continued on next page.)

OTHER PUBLICATIONS

Bhatta, N., M.D., et al., "Injury and Adhesion Formation Following Ovarian Wedge Resection with Different Thermal Surgical Modalities," *Lasers in Surgery and Medicine* 13:344–352 (1998).

Mecke, H., et al., "Incidence of adhesions following thermal tissue damage," *Research in Experimental Medicine* © Springer–Verlag (1991).

Mohsen, Amr A.., M.D., "Endocoagular Control of the Mesoappendix for Laparoscopic Appendectomy," *Journal of Laparoendoscopic Surgery*, vol. 4, No. 6 (1994).

Semm, K., "New Methods of Peliscopy (Gynecologic Laparoscopy) for Myomectomy, Ovariectomy, Tubectomy and Adnectomy," *Endoscopy 2*, George Thieme Publishers, (1979) 85–93.

*Primary Examiner*—Roy D. Gibson

(57) ABSTRACT

Systems and methods for reducing or minimizing post-surgical complications are described. By applying energy to tissues under specifically controlled conditions, the formation of adhesions in response to cutting or other damage of those tissue may be eliminated or significantly reduced. According to an embodiment of the method of the invention, energy application is controlled to heat the tissue within a range of 61 to 100 degrees centigrade. In one embodiment, the system of the invention includes an easily manipulated applicator, having a scissor-like configuration and a controller for the energy application.

45 Claims, 11 Drawing Sheets

U.S. PATENT DOCUMENTS

| | | |
|---|---|---|
| 5,914,345 A | 6/1999 | Slepian et al. |
| 5,944,718 A | 8/1999 | Austin et al. |
| 5,951,549 A * | 9/1999 | Richardson et al. .......... 606/45 |
| 5,971,980 A | 10/1999 | Sherman |
| 5,992,418 A | 11/1999 | de la Rama et al. |
| 6,004,547 A | 12/1999 | Rowe et al. |
| 6,050,996 A * | 4/2000 | Schmaltz et al. ............. 606/51 |
| 6,071,956 A | 6/2000 | Slepian et al. |
| 6,152,923 A * | 11/2000 | Ryan ............................ 606/51 |
| 6,231,569 B1 * | 5/2001 | Bek et al. ...................... 606/34 |
| 6,334,860 B1 * | 1/2002 | Dorn ............................ 606/48 |
| 6,338,731 B1 | 1/2002 | Laufer et al. |
| 6,517,536 B2 * | 2/2003 | Hooven et al. ................ 606/41 |

* cited by examiner

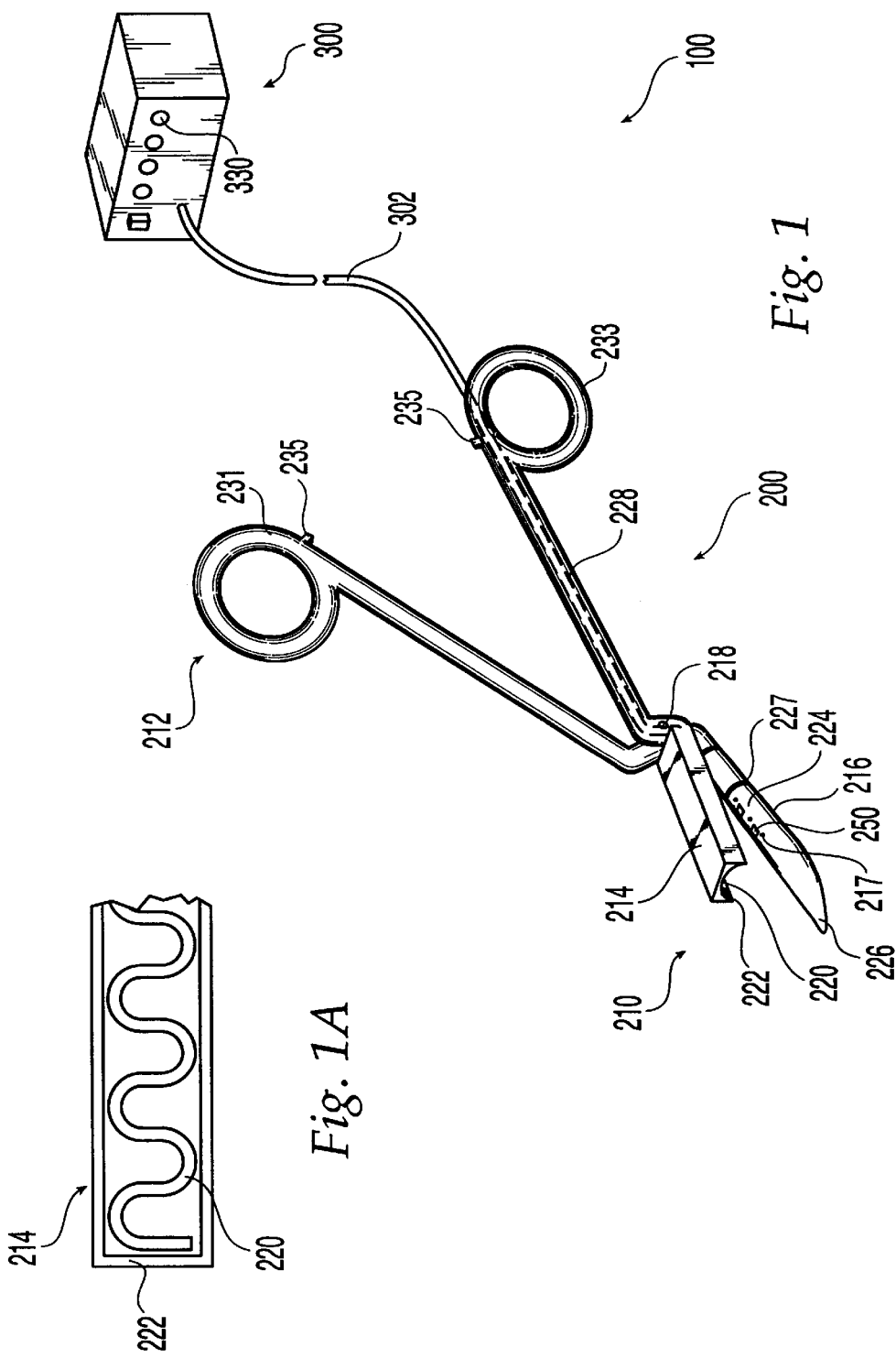

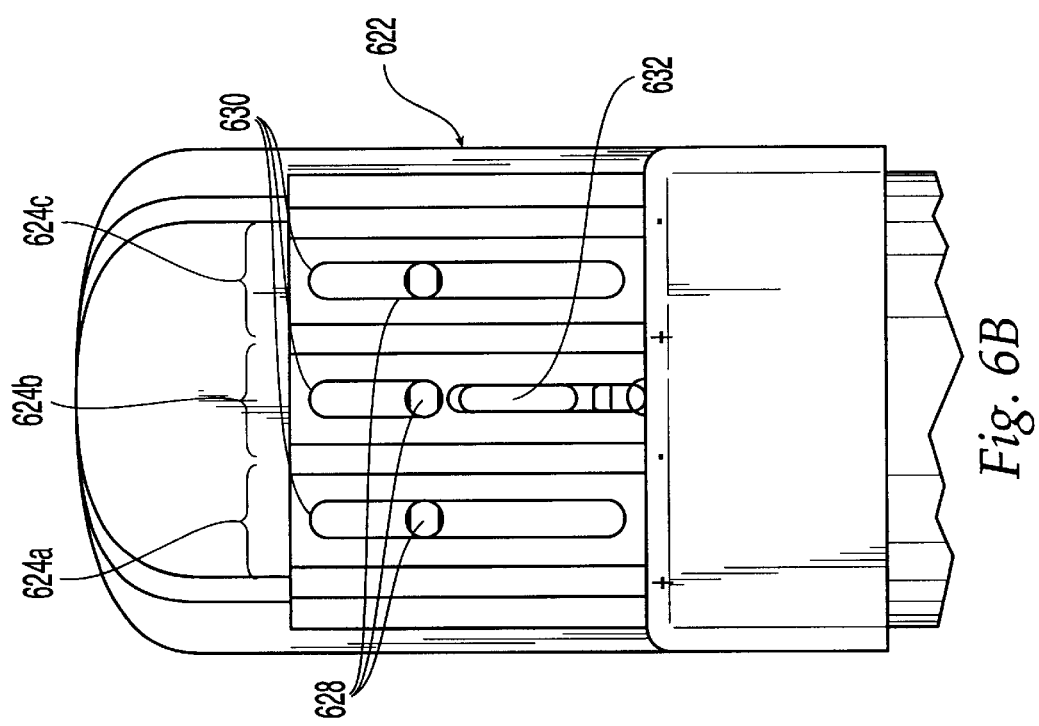

SYSTEM AND METHOD FOR REDUCING POST-SURGICAL COMPLICATIONS

This application claims the benefit of Provisional Application No. 60/271,475, filed Feb. 26, 2001.

FIELD OF THE INVENTION

The present invention generally relates to systems and methods for reducing the incidence of post-surgical complications. In particular, the present invention relates to tissue treatment systems and methods thereof for reducing post-surgical tissue adhesions at incision sites and/or at other sites distal thereto by treating the tissues prior to the incision thereof.

BACKGROUND OF THE INVENTION

As a result of the healing process that follows abdominal, pelvic, cardiothoracic, or orthopedic surgery, complications frequently arise due to the natural tendency of the body to form adhesions, which are typically connective tissue structures that form between injured areas within body cavities. Adhesions may form regardless of the nature of surgical procedures, whether done in a so-called minimally invasive fashion using laparoscopy or with a standard technique involving one or more relatively large incisions. These tissue bridges may cause various, often serious, complications. Relieving the post-surgical complications caused by adhesions generally requires another surgery. However, the subsequent surgery is further complicated by adhesions formed as a result of the previous surgery. In addition, the second surgery is likely to result in further adhesions and a continuing cycle of additional surgical complications.

One example of a problem that can be caused by adhesions is that following abdominal surgery loops of intestine may become entangled or twisted about these adhesions. The entanglements cause partial or total flow obstruction through the bowel or may compromise the blood flow to and from the bowel. If such a condition is not relieved rapidly, the bowel dies and shortly thereafter the condition may cause death of the afflicted patient. Another problem due to adhesions is infertility in women. Adhesions that form after gynecological surgery, especially tubal surgeries and myomectomies, are a common cause of infertility. Adhesions can form between the ovaries, fallopian tubes or pelvic walls. These adhesions can block the passage of ovum from the ovaries into and through the fallopian tube. Adhesions around the fallopian tubes can also interfere with sperm transport to the ovum, thus resulting in infertility. Another common problem after abdominal or pelvic surgery in women is pelvic pain due to post-surgical adhesions.

Various suggestions have been made to avoid, reduce, and/or eliminate the formation of adhesions. For instance, standard surgical procedures in the United States often include the steps of using powder-free gloves, washing powder from gloves prior to surgery, and washing body cavities thoroughly prior to closing incisions. Another of the strategies that has been suggested to prevent adhesion formation is to loosely place a non-reactive barrier between an injured peritoneal surface and internal organs. Materials such as Interceed™ and Seprafilm™ and methods as described in U.S. Pat. No. 5,791,352 to Reich et al. have been advocated for minimizing adhesions. Also pourable substances (solidifying liquid gel material) have been used to prevent adhesion formation. These measures, unfortunately, have had only modest success in reducing the formation of post-surgical adhesions at the surgical locations.

Therefore, there exist needs for new tissue treatment systems and methods thereof that would eliminate or minimize post-surgical adhesions.

SUMMARY OF THE INVENTION

The present invention generally relates to systems and methods for reducing the incidence of post-surgical complications. In particular, the present invention relates to tissue treatment systems and methods thereof for reducing post-surgical tissue adhesions at incision sites and/or at other sites by treating the tissues prior or substantially prior to the incision thereof.

In one aspect of the present invention, a method to reduce post-surgical adhesions includes steps of applying energy at a surgical incision site in a controlled manner, measuring or monitoring a parameter indicative of an amount of energy applied at the incision site, and applying the energy until the measured parameter corresponds to a value that indicates the energy application will result in a reduction in post-surgical adhesions. The energy may be applied on one or two surfaces of the tissue at the incision site. In a preferred embodiment the tissue is then cut after the adhesion reduction treatment, along the areas of tissue treated. The parameter measured may include tissue impedance, duration of energy application, tissue temperature, rate of change of tissue temperature, tissue appearance, or a combination of any of these parameters.

In a further embodiment of the invention a system for treating tissue to reduce post-surgical adhesions includes a first member configured to be placed on one surface of the tissue to be treated and a second member configured to be placed on an opposite side of the tissue to be treated, to back up the first member. A treatment element is disposed on at least one of the first and second members. The treatment element is configured to deliver energy to the tissue. Actuating means is provided to move the first and second members from an open to a closed position wherein the members and thus the treatment element are brought into apposition to the tissue. A control means, which may include a processor, is configured to preferably provide precisely controlled treatment parameter(s) through the treatment element in a manner which reduces post-surgical complications when the tissue thus treated is cut.

Alternatively, a system may also have one tissue contacting member on which at least one treatment element is disposed. In a situation where only one side of the tissue can be contacted, e.g., the anterior abdominal wall during laproscopic surgery, the tissue contacting member can provide the desired treatment through the treatment element(s).

According to a further preferred embodiment, the first or second member is provided with at least one sensor which measures at least one parameter, which may include the temperature of the tissue, amount of energy generated by the treatment element, amount of energy delivered to the tissue, the impedance of the tissue, or the appearance of the tissue.

Other features and advantages of the invention will be apparent from the following detailed description and from the appended claims.

BRIEF DESCRIPTION OF THE DRAWINGS

FIG. 1 is a schematic diagram of an exemplary tissue treatment system according to the present invention;

FIG. 1A is a bottom plan view of an upper jaw member showing a treatment element of the present invention;

FIG. 6B is a detailed plan view of the treatment element of the apparatus of FIG. 6A;

DETAILED DESCRIPTION OF THE INVENTION

Figure 1B:
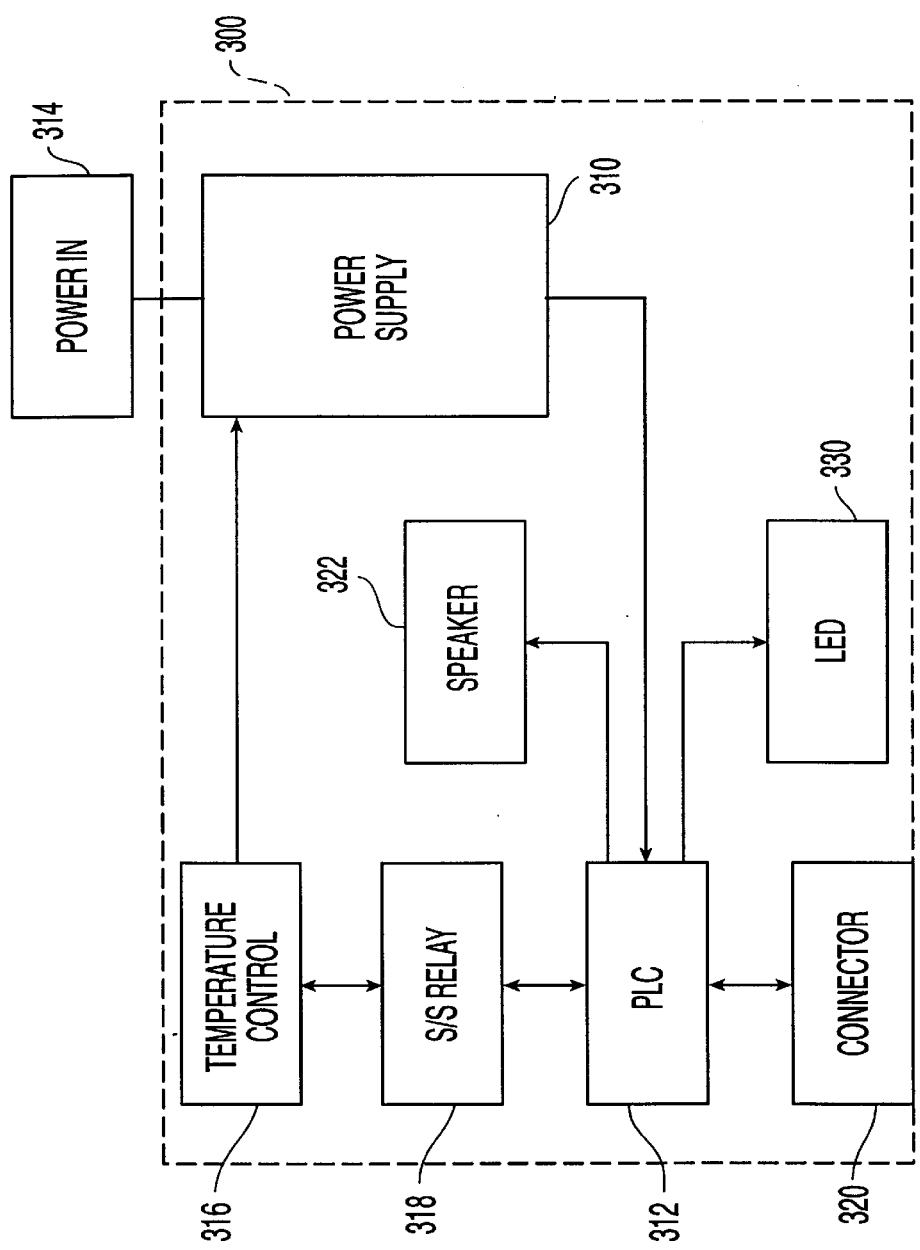
FIG. 1B is a block diagram of a controller according to one embodiment of the invention.

The following description provides systems and methods for reducing post-surgical complications. More particularly, the following description provides embodiments of tissue treatment systems and methods thereof for reducing post-surgical tissue adhesions at surgical sites. As used herein surgical sites refers to areas surrounding incision sites and/or other sites distal to the incision site at which there is a risk of adhesion formation.

While not intending to be bound by theory, it is believed that tissue treatment system of the present invention minimizes or reduces formation of post-surgical adhesions by inhibiting release of adhesion-inducing substances (which are believed to be growth factors, such as transforming growth factors, TGF-b, plasminogen activator inhibitor type-1, and/or urokinase plasminogen activator, etc.) from the injured tissues and/or adjacent lymphatic tissues. Therefore, a treatment element and controller, as described in greater detail below in connection with the various preferred embodiments of the invention, are preferably configured to apply energy to tissues at the surgical site so that such tissues are heated to and maintained at a predetermined temperature for a pre-selected duration in order to create such inhibition. Although the exact extent of thermal treatment in different portions of tissue may be quantitatively assessed by solving a generalized unsteady-state heat conduction equation with its boundary layer(s) maintained at a certain temperature, it may require a priori estimation of various mechanical properties of the tissue, e.g., anatomical structure of each cell, distribution of sub-cellular elements therein, thermal conductivity of each element of the tissues, thickness of the tissue layer, and the like. A more readily applied approach is to apply energy to one surface of the tissue (e.g., an upper or outer surface) and to measure the changes in the temperature on the opposite surface (e.g., a lower or inner surface). Because in a preferred embodiment, energy is delivered from the one surface toward another surface of the tissue, a temperature gradient is generated within the tissue and each portion of the tissue may be heated at different temperature. However, by appropriately selecting a target temperature, at least a substantial portion of the tissue can be treated to alter the release of the foregoing adhesion-inducing substances.

In general, a treatment element according to the present invention is controlled to deliver a predetermined amount of energy to the tissue to be treated, generally between about 45 to about 125 joules, and more preferably between about 60 to 75 joules. The energy delivery should be accomplished so as to not dessicate or otherwise damage the tissue. In order to avoid tissue damage, the tissue impedance preferably will remain about constant (with fluctuations throughout the treatment of as much as ±30%). However, to the extent overall tissue impedance in the treatment area increases due to the treatment, it should not increase more than about 100%. Increases of tissue impedance above this level indicate tissue dessication.

Energy input to the tissue according to the present invention may be conveniently monitored as a function of tissue temperature and time of treatment. In general, tissue to be treated is heated in pre-selected temperature ranges, e.g., broadly between 61° C. and 100° C., more specifically between 65° C. and 90° C., preferably between 70° C. and 80° C. or more preferably at about 75° C., for a pre-selected treatment duration, generally less than about 60 seconds. Preferably, the desired treatment temperature will be maintained for about 5–15 seconds, more preferably about 10 seconds. It is appreciated that the amount of energy delivered from the treatment element to the tissues is generally proportional to the thermal conductivity of the tissue (inversely proportional to impedance), temperature difference between the treatment element and the tissue, and treatment duration, but is inversely proportional to the thickness of the tissue. Accordingly, higher temperature on the surface of the treatment element may shorten the required duration of the treatment, though the correlation may not necessarily be a linear one. The treatment duration may also be shortened by heating the tissues from both the upper and lower surfaces thereof. In such an embodiment, the tissue temperature may be measured in the regions of the surgical site not covered by a treatment element. Another approach is to apply energy to one tissue surface and analyze the rate of changes in the temperature on the opposite tissue surface. Because a percentage change in the surface temperature is indicative of the change in temperature in the interior portions of the tissues, the treatment may be applied until the percentage change reaches a pre-selected threshold. Another alternative is to apply a series of treatment in short intervals (e.g., every 3, 5 or 10 seconds), to measure the temperature or other properties of the tissues, and to terminate the treatment when the temperature reaches the pre-selected value.

Referring now to FIG. 1, an exemplary tissue treatment system 100 according to the present invention is arranged to provide energy to tissues at a surgical site prior to the incision thereof, thereby reducing or minimizing post-surgical adhesions of tissues. Exemplary tissue treatment system 100 comprises applicator 200 and controller 300. Applicator 200 may be a scissors-like device with treatment portion 210 and handle portion 212. Treatment portion 210 includes upper energy application jaw 214 and lower support/sensor jaw 216, which pivot at hinge 218. Applicator 200 is connected to controller 300 via cable 302. Controller 300 includes an energy source as described in greater detail below.

Treatment portion 210 is designed to facilitate positioning of treatment member 220 (See FIG. 1A) on one or both of the upper and lower surfaces of tissue at the incision site to deliver energy to such tissue. Upper and lower jaws 214 and 216 include matching inner surfaces 222 and 224 such that tissue can be positioned and held therebetween. In the embodiment of FIG. 1, inner surfaces 222 and 224 of jaws 214 and 216 have matching arcuate contours and may be provided with corrugated or jagged or grooves 217 increase contact area to help hold and treat tissue. Lower jaw 216 may be shaped and sized to form a pointed distal tip 226, which may be used to puncture the tissues to provide an insertion site as described in greater detail below. Upper and lower jaws 214 and 216 may be provided with one or more markings 227 indicating a depth of insertion, thereby aiding the user to position lower jaw 216 to a pre-selected depth underneath the tissues. In general, upper and lower jaws 214 and 216 and/or their inner surfaces 222 and 224 may be arranged to have similar shapes and sizes for optimal mating. If preferred, however, the inner surfaces may also be arranged to have different, non-mating configurations to provide different areas of contact with the tissues.

One or more treatment elements 220 may be provided on one or both of upper and lower jaws 214 and 216. Treatment element 220 may be disposed on inner surfaces 222 and 224, in order to contact the surfaces of the tissue, and directly deliver heat thereto. As shown in FIG. 1A, in a preferred embodiment, treatment element 220 is a thin film resistive heating element disposed on arcuate inner surface 222 of upper jaw 214. Such an embodiment is generally preferable for non-radiative heating units, e.g., resistive heaters. In the alternative, treatment element 220 may be a radiative or RF heating unit disposed within the material of the jaws, spaced from inner surfaces 212 and 224 and deliver energy to the tissues. Treatment element 220 receives energy from controller 300 through connecting wire 228 and connection cable 302.

The shape and size of jaws 214 and 216 is determined by factors such as area and/or thickness of the tissues to be treated, type of the tissues, type and capacity of treatment element 220, preferred amount of energy to be delivered to the tissues, desired heat-sink properties, and the like. Jaws 214 and 216 may be made of any materials that are biomedically compatible and which are generally not degradable throughout the repeated use thereof. In general, selection of configuration and material for applicator 200 is a matter of choice of one of ordinary skill in the art.

Handle portion 212 is arranged to provide a means for the user to operate applicator 200 of tissue treatment system 100, i.e., to move jaws 214 and 216 of treatment portion 210 toward the tissues at the incision site, to position treatment element 220 adjacent to the incision site, and to hold tissue therebetween. Exemplary handle portion 212 in FIG. 1 includes a pair of handles 231 and 233 movably coupled to each other by a hinge 218. Handles 231 and 233 are arranged to rotate about hinge 218 along an arcuate path between an open position and a closed position so that an arcuate movement of handles 231 and 233 is transduced into another arcuate movement of jaws 214 and 216 between their open and closed positions. Locking mechanism 235 may be provided for the user to lock handles 231 and 233 at the closed position so that the tissues can be firmly held by jaws 214 and 216.

One or more sensors 250 are disposed in one or both of upper and lower jaws 211 and 213 to monitor various operational parameters related to the foregoing tissue treatment. Sensors 250 are electrically connected to controller 300 through connecting wire 228 and connection cable 302, transmit measurement signals thereto, and/or receive power from controller 300 to operate sensors 250. Any conventional sensors may be employed to measure an amount of energy generated by treatment unit 220 or delivered to the tissues, changes in tissue temperature at the incision site or sites adjacent thereto, and/or changes in other tissue properties resulting form the treatment. Examples of such tissue properties to be monitored may include, but not limited to, the temperature on the surfaces of the tissues at the incision site, temperature inside such tissues, temperatures in or on the tissues distal to the incision site, electrical resistance or impedance of the tissues, thermal conductivity of the tissues, tissue dimension such as length or thickness, tissue colors, and so on. Examples of sensors for measuring such tissue properties may include, but not limited to, thermistors, thermocouples, optical sensors, and the like.

Controller 300 includes an input/output unit (not shown) to receive various operational or measurement signals from sensors 250 and to transmit command signals to various parts of applicator 200. In a preferred embodiment, controller 300 provides the source of precisely controlled energy to treatment element 220. This may be as straight forward as controlled power to a resistive heating element or more complex generation of radio-frequency waveforms. Controller 300 is preferably provided with multiple LED indicators 330 representing specific modes of operation examples of which may include system ready, system failure, initiation of treatment, progression of treatment, completion of treatment, and the like. Sound indicators may also be used independently or in conjunction with foregoing light indicators 330. In addition, an optional monitor or display screen may be provided to display such modes of operation or measured tissue temperature or properties as well.

Controller 300 may manipulate operation of treatment element 220 and/or other parts of applicator 200 manually (e.g., according to user commands) or automatically (e.g., by a processor implemented control algorithm). Such control algorithm may allow controller 300 to initiate or terminate the foregoing treatment upon occurrence of one or more pre-selected events. For example, controller 300 may initiate the treatment upon detecting the tissues positioned adjacent to or between jaws 214 and 216. Controller 300 may automatically terminate the treatment, e.g., after lapse of a pre-determined amount of time, after delivering a pre-determined amount of energy to the tissues, and/or after detecting pre-selected change in the tissue temperature or other tissue properties measured by foregoing sensor 250.

Controller 300 may also be arranged to enable the user to adjust treatment parameters such as, e.g., duration of treatment, amount of energy generated by treatment element 220 or delivered to the tissues, temperature of the tissues, resistance or impedance of the tissues, and other tissue properties. In the alternative, controller 300 may be arranged to adaptively determine optimal treatment parameters and operate treatment element 220 accordingly, e.g., by comparing temperature and/or other properties of the tissues being treated with those of the distal tissues through processor implemented contact schemes. In a preferred embodiment, controller 300 will also provide safety control, such as by continuously monitoring critical parameters and initiating an alarm or terminating treatment if such parameter does not conform to predetermined criteria. Although controller 300 is generally provided as a stand-alone unit, it may be constructed as a microchip incorporating the foregoing control algorithms and implemented directly within applicator 200.

Additional position sensors may also be disposed on treatment or handle portions 210 and 212. These position sensors may be coupled with controller 300 so that they may initiate and/or terminate the foregoing tissue treatment automatically based on the relative locations of upper and lower jaws 214 and 216 and/or those of handles 231 and 233.

Controller 300 may further be arranged to generate a variety of visual and/or audible warning signals when applicator 200 is not in ready position and/or when the tissues positioned between jaws 214 and 216 can not be properly treated. For example, by monitoring the signals generated by the foregoing position sensors, controller 300 may send a warning signal when upper and lower jaws 214 and 216 are not in their fully closed position or when the tissues positioned therebetween exceed a pre-selected threshold thickness. In such cases, treatment element 220 and/or controller 300 may not be able to complete the tissue treatment regardless of the duration of the treatment. Therefore, controller 300 is preferably configured not to initiate the tissue treatment regardless of the user command. In addition, controller 300 may be arranged to warn the user when the changes in the tissue temperature and/or other tissue properties do not reach the pre-selected value after a certain period of time. This embodiment would prevent an incomplete tissue treatment that may be inadvertently followed by the incision thereof. A self-calibration circuit may be provided to various electronic parts of applicator 200 so that the tissue treatment may not be initiated when applicator 200 is in a faulty condition.

One example of a controller according to a preferred embodiment of the invention is illustrated in FIG. 1B. In this embodiment, controller 300 includes power supply 310 and programable logic controller (PLC) 312. Power supply 310 receives power from power source 314 to regulate the power supply for the controller. Power source 314 may be, for example, internal or external batteries, or a wired connection to a source of power. Temperature controller 316 and solid state relay 318 comminicate with PLC 312 to control the temperature applied by the treatment element(s) based on the predetermined treatment algorithm and signals received from the sensor(s). Connection to cable 302 and thus the treatment element(s) is via connector 320, for example a ten-pin connector. In order to provide feedback to the user, speaker 322 and LEDs 330 are controlled by PLC 312 to provide audio and visual signals indicative of the state of treatment. It will be appreciated by persons of ordinary skill in the art based on the teachings provided herein that other suitable controllers may be devised, whether based on microprocessor control or analog circuitry, in order to effect the treatment according to the invention.

Figure 1C:
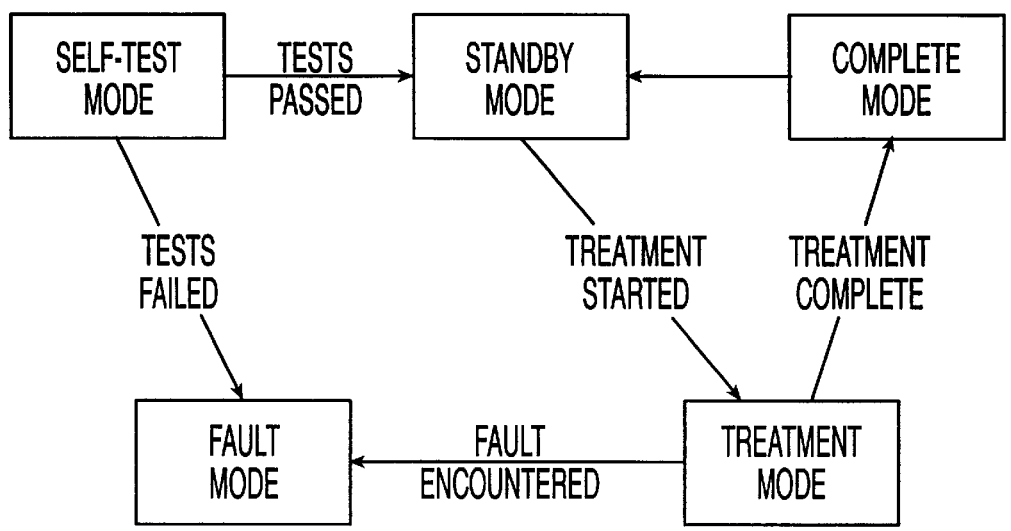
FIG. 1C is a state diagram illustrating different control modes according to one embodiment of the invention.

According to a further exemplary embodiment of the invention, controller 300 operates in one of five modes, (1) SELF-TEST, (2) STANDBY, (3) TREATMENT, (4) COMPLETE, and (5) FAULT as shown in FIG. 1C. The SELF-TEST Mode mode occurs automatically upon power up. In the SELF-TEST Mode, the control unit automatically runs self-diagnostics in order to determine if the controller itself and the treatment element are functioning properly. This mode automatically transitions to STANDBY mode after an applicator, such as applicator 200, has been connected to the controller and found to be functional by the controller. In the STANDBY mode a green LED 330 is illuminated on the controller. This mode is automatically entered after either the SELF-TEST or COMPLETE modes. The STANDBY Mode indicates that the system is ready for energy delivery according to the desired treatment. When utilized with applicator 200, the STANDBY mode preferably can be exited only by closing jaws 214 and 216. In the TREATMENT Mode energy is delivered to the selected tissue. A yellow LED 330 is illuminated on controller 300 and an audible tone of one beep per second is preferably indicated in this mode. This mode is initiated after closing the jaws in applicators 200 and 600. Initiation may be accomplished manually by activating a button on the controller or a switch on the applicator, for example switch 604 on applicator 600, shown in FIG. 4. At the completion of TREATMENT mode, a four beep in one second tone signals the termination of the treatment. The TREATMENT mode can be exited when the treatment is complete or a FAULT mode occurs. If the TREATMENT mode is exited when the treatment is complete, the COMPLETE mode is automatically entered. The COMPLETE Mode transitions automatically into STANDBY. The FAULT Mode indicates that an error has occurred. Red LED 330 is illuminated on the controller in this mode. Information on trouble shooting fault conditions may be displayed on an optional display or converted through LED/Audio signals correlated to predetermined fault signals and explained in associated documentation.

Figure 2A:
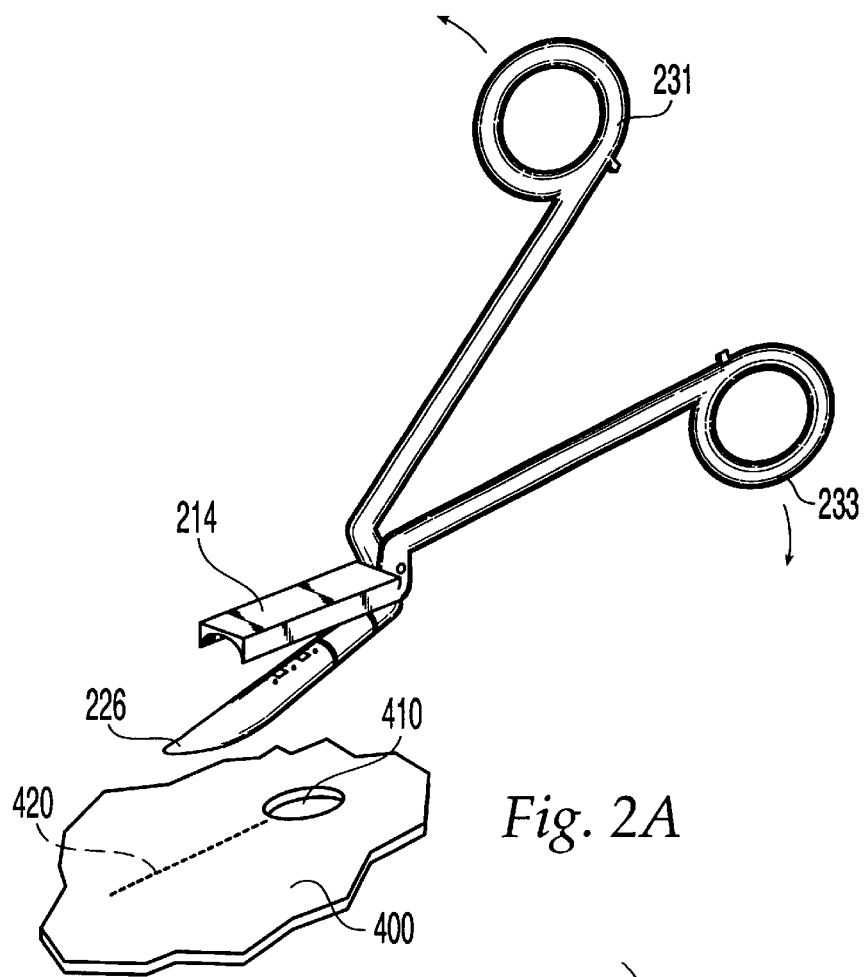
FIG. 2A is a schematic diagram of the tissue treatment system of FIG. 1 in an open position according to the present invention.
Figure 2B:
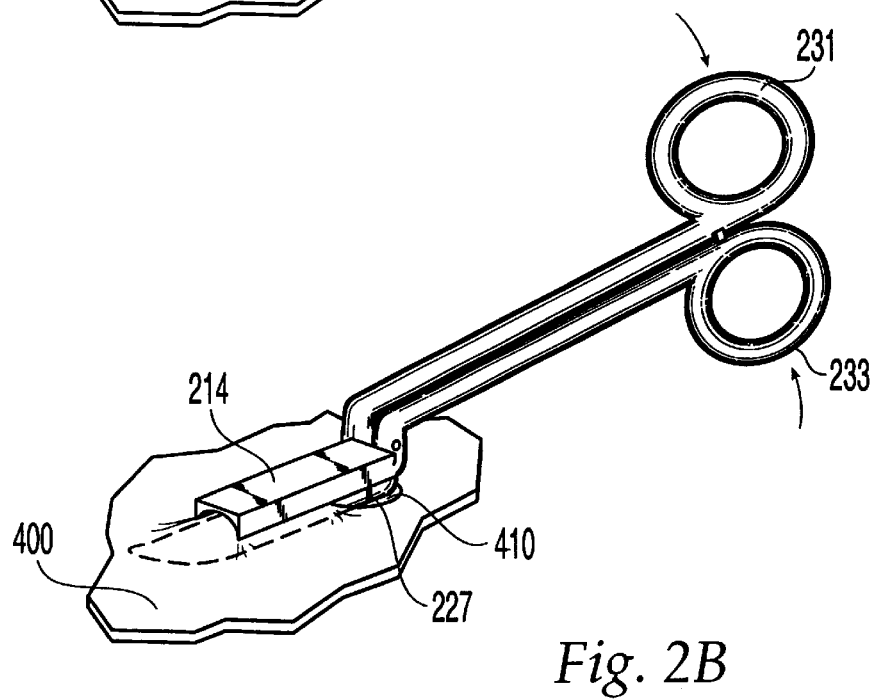
FIG. 2B is a schematic diagram of the tissue treatment system of FIG. 1 in a closed position according to the present invention.

FIGS. 2A and 2B are schematic diagrams of the tissue treatment system of FIG. 1 in an open and closed position, respectively, according to the present invention. In operation, applicator 200 is removed from a sterilized package and connected to controller 300 by connection cable 302. Controller 300 is turned on and initialized at proper settings for the tissue treatment. A small hole is cut in tissues 400 adjacent to or at the extension of an surgical site 420 in order to provide an insertion hole 410 for receiving lower jaw 216 of applicator 200. According to a preferred embodiment of the invention, tissue 400 represents the peritoneum after the overlying tissues such as fascia and muscle have been incised and retracted. Thus, in a preferred embodiment, the treatment described is applied directly to the peritoneum. The size of insertion hole 410 is approximately 3 mm long which may, however, vary depending on the size of lower jaw 216. As shown in FIG. 2A, handles 231 and 233 are moved to their open position such that upper and lower jaws 214 and 216 are separated and moved to their open position. As shown in FIG. 2B, distal tip 226 of lower jaw 216 is then inserted through insertion hole 410 and entire lower jaw 216 is slid along the lower surface of the tissues until the edge of insertion hole 410 reaches at pre-selected marking 227 of lower jaw 216. It is preferred that upper and lower jaws 214 and 216 be positioned directly on and below the tissues to be treated, respectively such that no intervening anatomical structures are trapped therebetween. After confirming the position of upper and lower jaws 214 and 216, handles 231 and 233 are moved to their closed position such that upper and lower jaws 211 and 213 are moved to their closed position as well, thereby holding the tissues therebetween. Locking mechanism 235 may be engaged to firmly hold the tissues between upper and lower jaws 214 and 216 and to prevent slipping of the tissues therefrom.

Once the tissues are properly positioned with respect to treatment element 220, the tissue treatment is initiated manually by the user or automatically by controller 300. As treatment element 220 commences energy delivery, tissue temperature or other tissue properties are monitored. When the tissue temperature or other tissue properties reach the pre-selected value as measured by sensors 250, treatment element 220 is disengaged and handles 231 and 233 are moved to their open position to release the tissues from the jaws 214 and 216. Lower jaw 216 is pulled back from insertion hole 410 and applicator 200 is removed from incision site 420. The treated tissues may then be cut along the insicion site by conventional techniques. Applicator 210 is then repositioned in a next site and the foregoing procedures are repeated as required.

Figure 3:
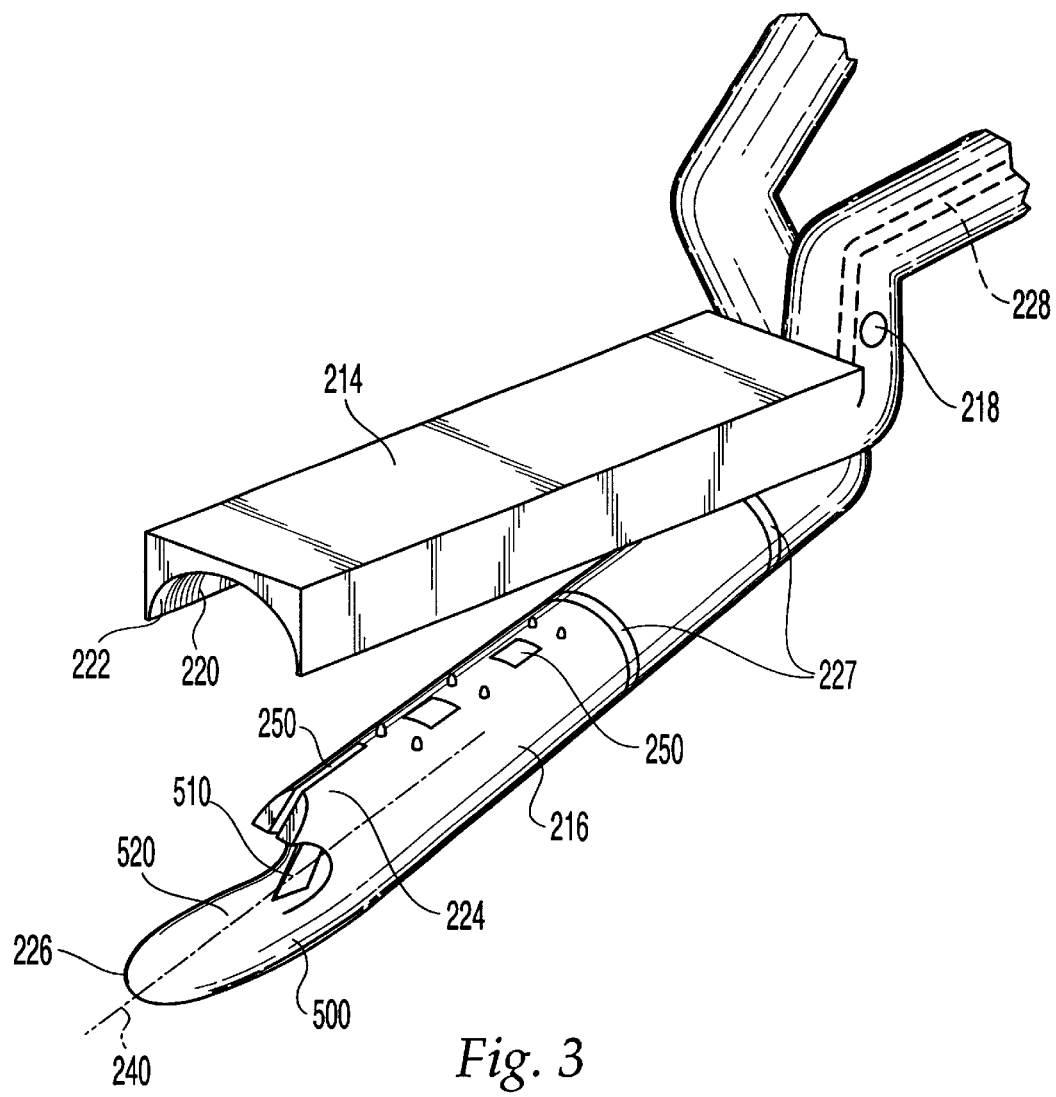
FIG. 3 is a schematic diagram of another exemplary tissue treatment system including an applicator with a cutting member according to the present invention.

In order to facilitate sequential tissue treatment and cutting, the foregoing tissue treatment system may incorporate a cutting member in either or both of the upper and lower jaws of the distal member of its applicator. FIG. 3 is a schematic diagram of another exemplary tissue treatment system including an applicator with a cutting member according to the present invention. Applicator 201 includes upper and lower jaws 214 and 216 which are as shown in FIGS. 1, 2A, and 2B, except that a cutting member 500 is provided on lower jaw 216. More specifically, cutting member 500 is disposed at a distal portion of lower jaw 216 and includes at least one cutting blade 510 and a cutter foot 520. Cutting blade 510 is generally disposed under inner surface 222 of upper jaw 214 in the closed position to prevent inadvertent cutting of the tissues during the treatment thereof. As will be discussed below, cutting blade 510 is also preferably arranged at an angle with respect to a longitudinal axis 240 of lower law 216 to facilitate cutting operation. Cutter foot 520 is generally provided between cutting blade 510 and distal tip 226 of lower jaw 216 to define a gap which is at least slightly greater than the thickness of the tissues to be cut. Cutter foot 520 may also be utilized as a guide to position distal tip 226 of lower jaw 216 immediately below the lower surfaces of the tissues.

In operation, the foregoing procedures are repeated so that treatment element 220 is positioned at incision site 420 and the tissues are treated thereby. After completion of the treatment, treatment element 220 is disengaged and handles 231 and 233 of proximal member 230 are moved to their open position to release the tissues from upper and lower jaws 214 and 216. Lower jaw 216 is slightly pulled back from insertion hole 410 until cutting blade 510 of cutting member 500 reaches edges of insertion hole 410. At this point, applicator 200 is tilted upward, while keeping cutting blade 510 in contact with the edges of insertion hole 410. When cutting blade 510 forms about a right angle with the edges of the tissues around insertion hole 410, applicator 200 is moved forward along incision site 420 and cuts the treated tissues while keeping cutting blade 510 centered within the band of the treated tissues. During the cutting operation, cutter foot 520 is manipulated to be in direct contact with the lower surfaces of the tissues and slightly lifted upward to prevent inadvertent capture and undesirable cutting of anatomical structures underlying the treated tissues. When cutting blade 510 approaches a boundary of a region of the treated tissues, lower jaw 216 of applicator 200 is reinserted underneath the lower surfaces of untreated tissues and the foregoing procedure is repeated to treat the tissues in the new incision site.

The foregoing cutting device may be disposed at locations different from the one described in FIG. 3. For example, cutting blade 510 may be disposed further toward distal tip 226, further proximal toward inner surface 224 of lower jaw 216 or at upper jaw 214. Cutting blade 510 may also be incorporated on the side of upper or lower jaw 216 as well. Alternatively, the upper jaw 214 may include a slit. Upon completion of tissue treatment, a cutting instrument, such as a scalpel, is introduced through the slit to contact the treated tissue. A linear cutting motion of the cutting instrument can then be used to precisely cut the treated portion of the tissue. In another embodiment of the tissue cutter, the opposing faces of the upper and lower jaws 214 and 216 have slots built into them. A cutting element, which is mechanically connected to the handle portion 231, can move linearly along the slots in jaws 214 and 216. When tissue is held between the jaws and the cutter is activated after completion of treatment, the tissue that is held between the jaws is precisely cut.

Figure 4:
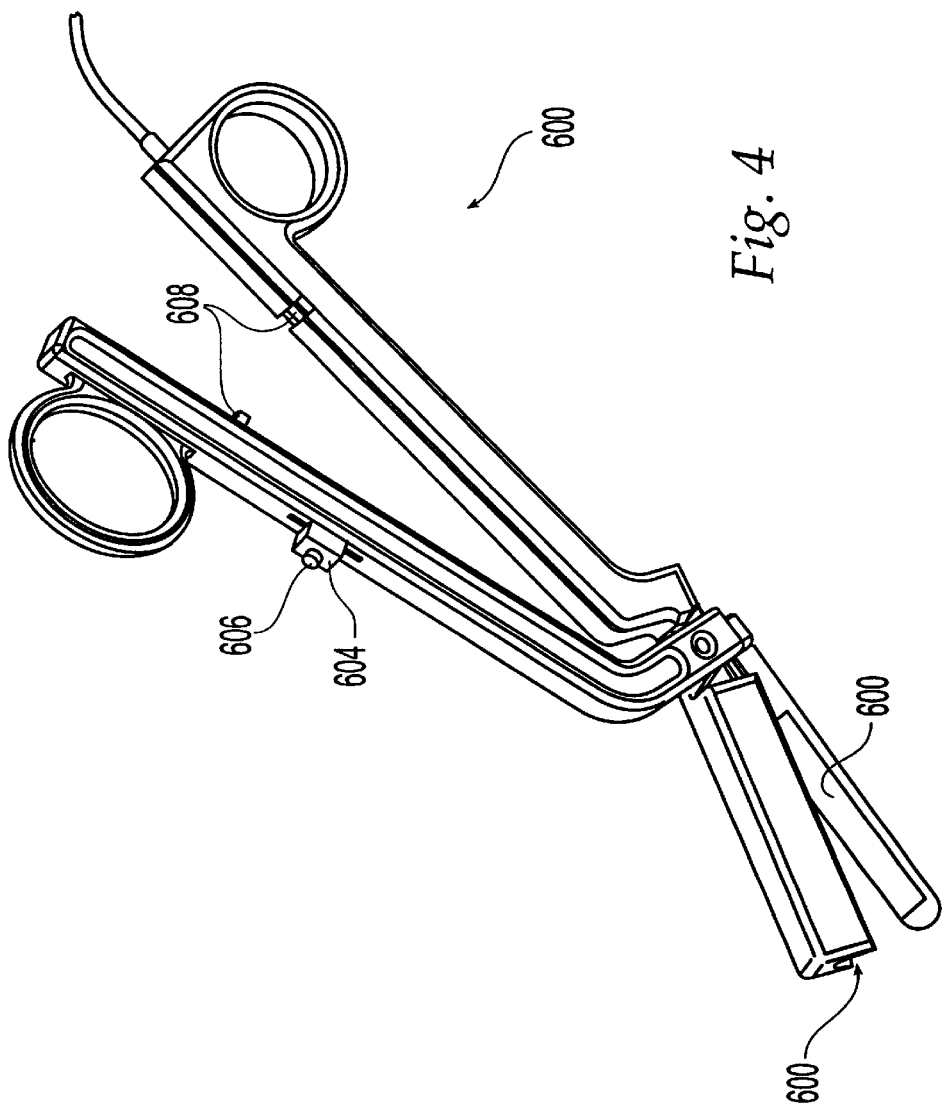
FIG. 4 is perspective view of an alternative treatment apparatus according to the present invention.

In a further alternative embodiment, a dual system for adhesion treatment and electrocautery is incorporated into applicator 600 as shown in FIG. 4 by including an ELECTRO CAUTERY mode in addition to other modes (See FIG. 1C). Applicator 600 is in many respects similar to applicator 200 and therefore only the areas of difference will be described in detail. Applicator 600 utilizes RF energy supplied by controller 300 and delivered to the tissue through RF electrodes 602. Electrodes 602 are positioned on the upper and lower opposed surfaces of the jaws of the applicator. As shown in FIG. 4, only the lower electrode 602 is visible, a mating electrode is disposed within the concave shape of the upper jaw. Electrodes 602 preferably run at least approximately along the length of the applicator jaws and may be made from a single wire or a wider ribbon. Alternatively, multiple electrodes, for example as described in detail below in connection with FIG. 6B, may be used on the upper and/or lower jaw. Applicator 600 is utilized in the same manner as applicator 200, except that after adhesion prevention treatment as described, selector switch 604 may be used to switch the applicator to an ELECTRO CAUTERY mode such that the incision may be made by electrodes 602 and cauterized in one step. For example, for adhesion treatment selector switch 604 is pushed forward with the user's thumb, signaling to controller 300 to deliver adhesion prevention treatment in accordance with the determined treatment scheme in the TREATMENT Mode. Selector switch 604 may include safety button 606, which must be depressed to permit movement of the switch. Once adhesion treatment is complete, the selector switch may be moved backward to signal controller 300 to deliver higher energy levels for electro cautery, as is known in the art. Safety switch 608 is included so that energy can only be delivered when the handles are firmly squeezed together.

Figure 5:
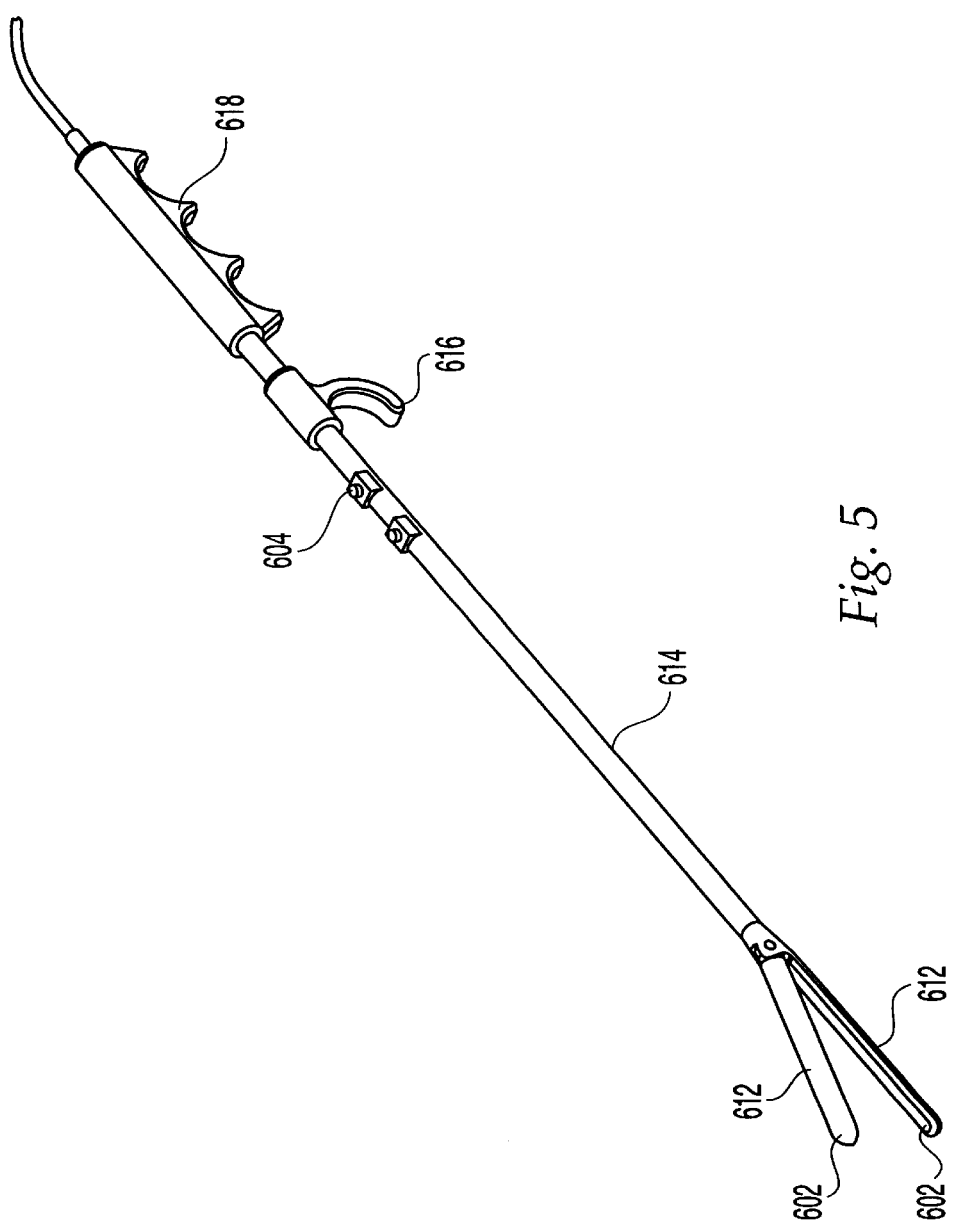
FIG. 5 is a perspective view of a further alternative embodiment of a treatment apparatus that is particularly suited for laparoscopic use according to the present invention.

In an alternative embodiment shown in FIG. 5, applicator 610 operates in the same general manner as applicator 600, but is configured for laparoscopic applications. In particular, jaws 612, which still include electrodes 602, are positioned at the end of elongate shaft 614 and are operable via trigger 616 by means of a suitable trigger mechanism. Shaft 614 may be rigid or flexible/malleable. Handle 618 provides a grip for the user by which the device is easily manipulated. Numerous suitable trigger mechanisms disclosed in the laparoscopic art and may be easily devised by a person of ordinary skill.

In a preferred embodiment, controller 300 automatically controls the adhesion treatment to completion, regardless of the position of selector switch 604, in order to prevent under-treatment or over heating of the tissue before the treatment is complete. According to the invention, excessive heat should not be applied before the prescribed treatment is complete, otherwise tissue damage that may result in adhesions can occur.

Figure 6A:
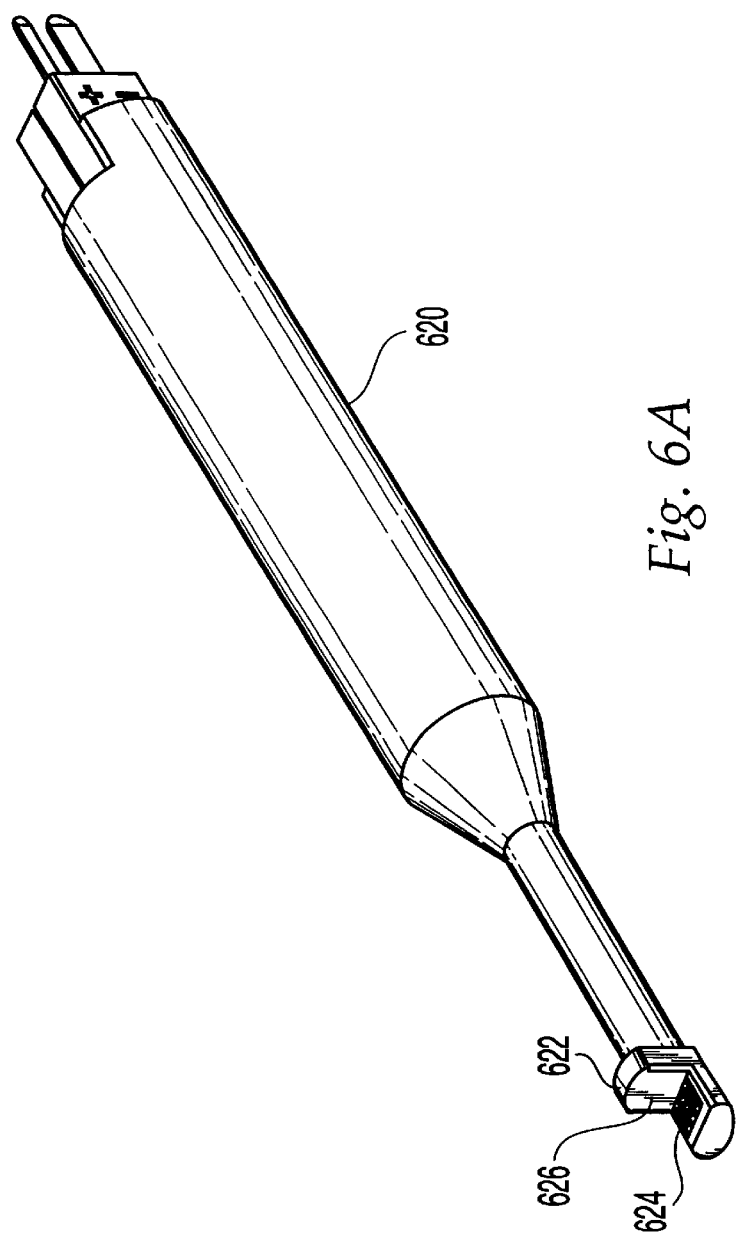
FIG. 6A is a perspective view of another alternative embodiment of the present invention utilizing RF electrodes.

In order to apply treatment to various body tissues in various orientations, a variety of applicators and treatment elements may be devised by persons of ordinary skill in the art based on the teachings contained herein. Exemplary embodiments of such alternative applicators are shown in FIGS. 6A–8. For example, wand applicator 620 is shown in FIGS. 6A and 6B. Distal end 622 of applicator 620 includes a multitude of RF electrodes 624. At the opposite, proximal end 626 appropriate connections are provided for connection to controller 300. Distal end 622 may assume any convenient shape to facilitate treatment application to particular tissue structures as desired. As shown in FIG. 6A, vertical wall 626 forms a notch-like structure to facilitate guiding electrodes 624 along a tissue edge. End 622 may also be flat.

As shown in FIG. 6B, in one alternative preferred embodiment, electrodes 624 are arranged in three controllable pairs 624a, 624b and 624c. As shown, electrodes are shared by adjacent pairs in the control logic. By spacing the active (+) and return (−) electrodes appropriately, the depth of penetration of the RF electric field can be controlled and hence the depth of the adhesion treatment that is created by the energy distribution. Irrigation ports 628 communicate with open irrigation channels 630. Irrigation can be used to facilitate surface temperature control in deeper tissue treatments and also helps prevent tissue from sticking to the electrodes. Temperature measuring means 632, such as a thermocouple, is preferably positioned among the electrodes in order to measure the temperature of the tissue contacted by the electrodes. The temperature values are reported to the controller, which, based on a preset algorithm as discussed above, can modulate the energy flow to the electrodes such that the treatment delivered to the tissue is precisely controlled for adhesion prevention.

Figure 7:
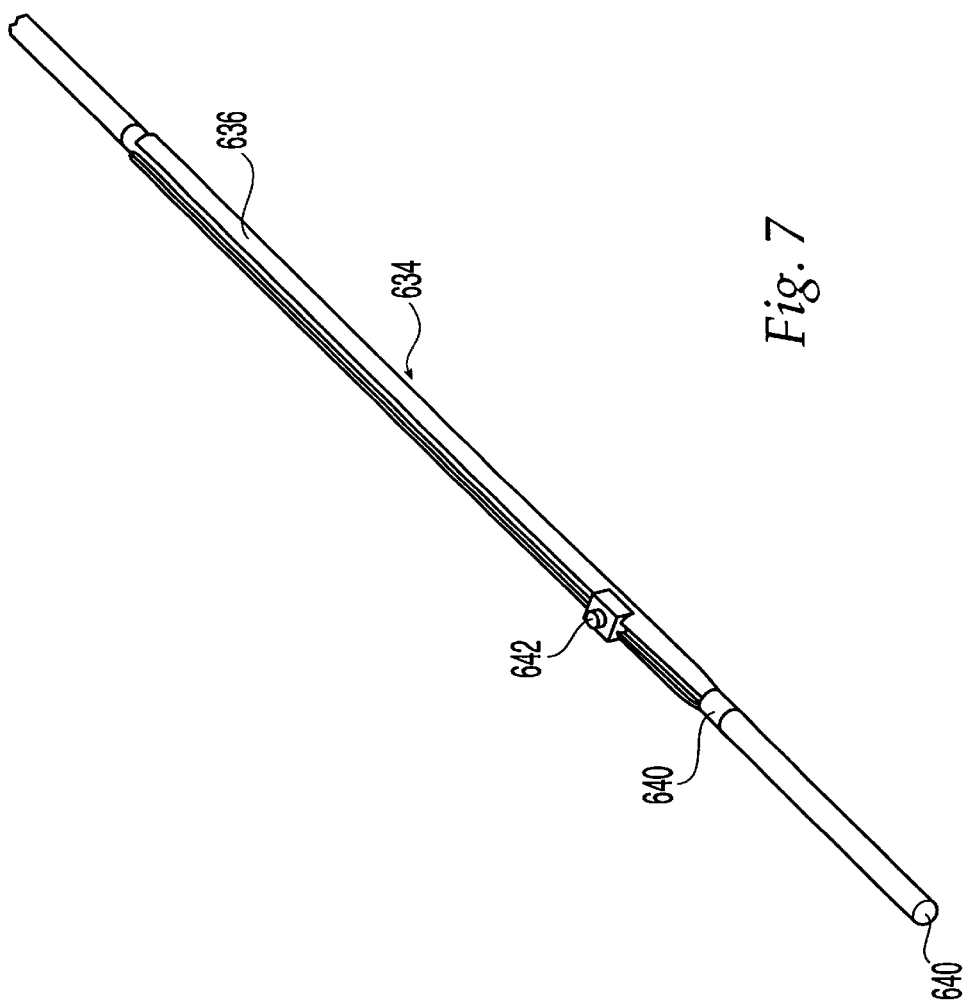
FIG. 7 is a perspective view of yet another treatment apparatus according to an alternative embodiment of the invention.

A further alternative applicator 634 is shown in FIG. 7. Applicator 634 is particularly useful for treating tissue laparoscopically and where only one side of the tissue is readily accessible. Applicator 634 is a wand-like device comprising a handle portion 636 and distal, preferably flexible, treatment element 638. Treatment element 638 may be a flexible, resistive heating element with a construction similar to treatment element 220, described above. One or more thermocouples 640 are disposed adjacent the treatment element for tissue treatment monitoring. The proximal end of applicator 634 includes appropriate connections to a controller such as controller 300. Finger operated control switch 642, for applying and terminating treatment, may be located any where along the length of handle portion 636. A more distal location provides greater control, while a more proximal location provides greater reach.

Figure 8:
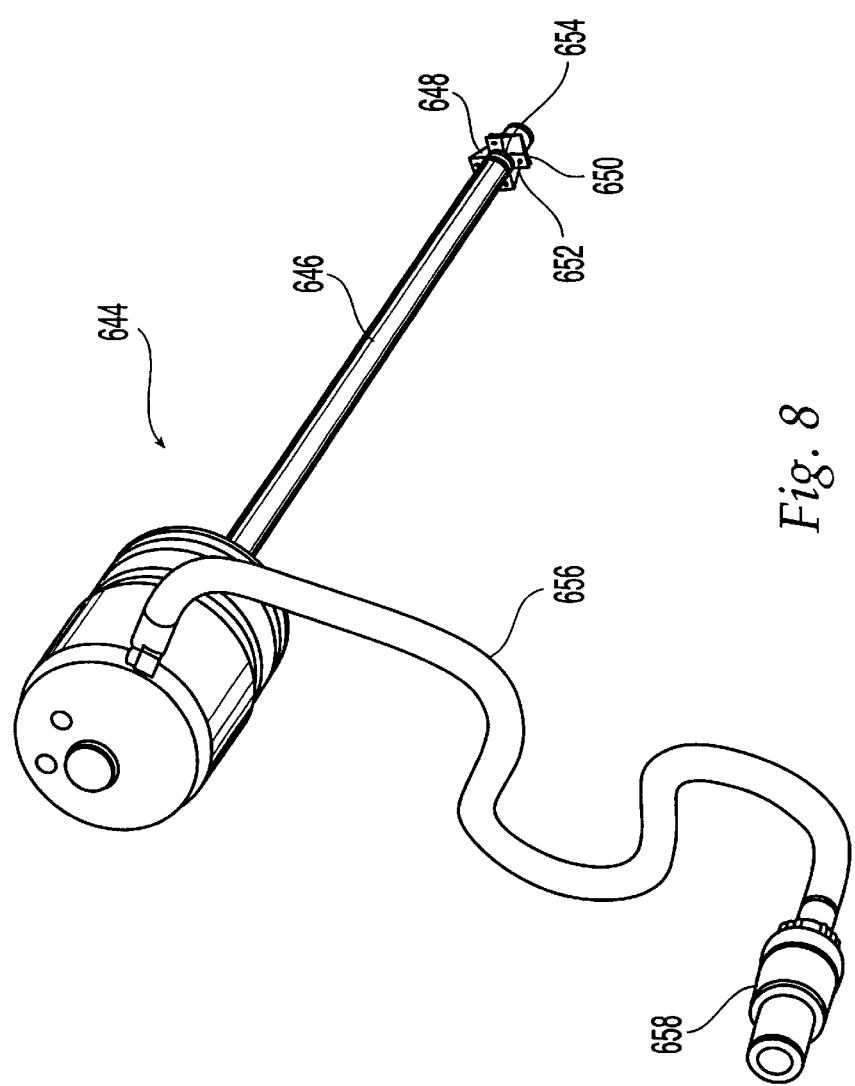
FIG. 8 is a perspective view of a further alternative embodiment of treatment apparatus according to the invention.

Applicator 644, shown in FIG. 8, is particularly useful for treating the back side or inside of tissue surfaces that are accessed, for example, by a trocar. Applicator 644 includes a shaft 646 with an expandable hinge 648 at the distal end. Shaft 646 may be a laparoscopic access cannula or a solid wand. Expandable hinge 648 includes outwardly expandable flanges 650 with treatment elements 652 disposed thereon. One example of a suitable expandable hinge for use with the present invention is disclosed in U.S. Pat. No. 5,232,451, which is incorporated by reference herein. As with other embodiments, a temperature sensing means is preferably disposed on proximity to the treatment elements to monitor the treatment application. As shown in FIG. 8, one or more thermocouples 654 are employed.

Treatment elements 652 may be either resistive heating elements or RF electrodes as previously discussed. When RF energy is to be used, the adjacent electrodes may be appropriately selected for bipolar operation. Cable 656 and connector 658 provide connection to a suitable controller, such as controller 300.

The various alternative embodiments of applicators according to the invention as described herein illustrate the principles of the invention. It will be appreciated by persons of ordinary skill in the art that treatment elements controlled according to the invention may be employed in a wide variety of surgical instruments other than the specific examples described herein above, without departing from the invention. Further examples include, but are not limited to, anastomosis devices, especially gastrointestinal anastomosis (GIA) devices and various surgical stapling devices. Generally, any surgical device which cuts, punctures or otherwise damages tissue, and which includes at least one tissue contacting surface on which a treatment element may be disposed, may be advantageously modified according to the present invention to reduce the incidence of post-surgical adhesions resulting from use of the device.

The following examples describe an exemplary tissue treatment system, methods thereof, and experimental results therefrom according to the present invention. The results clearly indicate that the foregoing treatment system substantially reduced the post-surgical complications in the animal models.

EXAMPLE 1

The exemplary tissue treatment system shown in FIG. 1 was constructed and applied to assess effects of tissue pre-treatment before surgical incision. Fourteen pigs each of which weighed around 25 kg underwent a standard laparotomy incision from the xyphoid to immediately above the umbilicus resulting in a 6 cm to 7 cm incision at the peritoneum. Out of fourteen pigs, ten pigs (treated group) were treated with tissue treatment system 500 as shown in FIG. 3 by heating the peritoneum thereof before making the incision with cutting tip 510 of tissue treatment system 500. The controller was set to maintain tissue temperature at 75° C. Upon the tissue reaching 75° C., the tissue that was held between the jaws was maintained at 75° C. for 10 seconds. After the incision of the peritoneum, a portion of small bowel was resected by an Endo GIA stapler (AutoSuture, United States Surgical Corp., Norwalk, Conn.). The remaining four pigs (control group) received the same surgery but without being treated by system 500.

Animals in both groups were sacrificed after 7 to 13 days and necropsy was performed. In addition, adhesions at various surgical sites were evaluated. For example, adhesions, if any, were assessed at the laparotomy incision site, surgical site, at the small bowel and any other location in the abdomen where adhesions were found. Each necropsy was videotaped and all adhesion evaluation data were recorded on case report forms. The results were analyzed by the Pearson Chi-Square test. Table 1 summarizes the results of adhesion evaluations at the incision sites.

TABLE 1

Summary of Adhesion Evaluations

| Adhesions | Control | Treated | Total |
|---|---|---|---|
| Yes | 3 | 0 | 3 |
| No | 1 | 10 | 11 |
| Total | 4 | 10 | 14 |

Out of four control animals, three (¾; 75%) developed adhesions to the incision sites, while none (%10; 0%) of the animals treated by tissue treatment system 500 developed adhesions thereto. The Pearson Chi-Square test revealed that the Chi-square was 9.545 and the control animals were 11 times (odds ratio) more likely to have adhesions than the treated animals. The statistical analysis confirmed that there existed a correlation between the occurrence of adhesion and treatment of tissues at the incision sites by tissue treatment system 500 (e.g., the p value was 0.002). No side effects or increased risks of treatment were noted in the study.

EXAMPLE 2

Effects of tissue treatment on the post-surgical complication were also tested in a total of twenty-two pigs, each weighing around 25 kg. The animals were randomized to the treated group (eleven) and control group (eleven), where each animal underwent the same standard laparotomy incision. For example, animals in the treated group received the same treatment by system 500 before the peritoneal incision and the bowel resection, while those in the control group underwent the same surgery but did not receive the treatment.

Animals were then sacrificed, necropsy was performed, and adhesions were evaluated. To ensure unbiased evaluation, the evaluator was blinded to the assignment of each animal. The necropsy was videotaped and the adhesion evaluation data were recorded on the case report forms. One of the control animals was excluded from the study due to a surgical complication that was unrelated to the treatment. Also, one treated animal developed adhesions, but that animal was also excluded from the statistical analysis because it appeared that the adhesions were the result of an infection communicated from the external incision site. As a result, the data for twenty animals (ten treated and ten control) were analyzed using the Pearson Chi-Square Test. Table 2 summarizes the results of adhesion evaluations at the incision sites.

TABLE 2

Summary of Adhesion Evaluations

| Adhesions | Control | Treated | Total |
|---|---|---|---|
| Yes | 4 | 0 | 4 |
| No | 6 | 10 | 16 |
| Total | 10 | 10 | 20 |

Four of the ten (4/10; 40%) control animals were diagnosed with adhesions to the incision site, compared to none of the ten (0/10; 0%) animals treated by tissue treatment system 500. The Pearson Chi-Square test revealed that the Chi-square was 4.997 and the control animals were 2.7 times (odds ratio) more likely to have adhesions than the treated animals. The statistical analysis also confirmed a correlation between the occurrence of adhesion and tissue treatment which was signified by the p value of 0.025 (0/10; 0%). No side effects or increased risks of treatment were noted in the study.

EXAMPLE 3

Effects of the tissue treatment on distal post-surgical complication were also analyzed in the animals of Example 2 (ten treated and ten control). While three of ten (3/10; 30%) control animals developed distal adhesions, none of the ten (0/10; 0%) treated animals did.

When the animals from Examples 1 and 2 were included in the analysis of adhesions to the incision site, a statistical correlation was also found. Combined data from both Examples 1 and 2 were stratified using the Cochran-Mantel-Haenszel (CMH) test. Seven of the fourteen (7/14; 50%) control animals developed adhesions to the incision site, whereas none of the twenty (0/20; 0%) treated animals did. The adjusted Pooled CHM value was 12.61 ($p \leq 0.001$), indicating a relationship between the incision adhesions and the tissue treatment according to the present invention. Table 3 summarizes the results of adhesion evaluations of the incision adhesions.

TABLE 3

Analysis of the Incision-Site Adhesions and Distal Adhesions

| | Adhesions to Incision Site | Distal Adhesions | p Value (adhesions to incision site) |
|---|---|---|---|
| Control (Ex. 1) | 75% | 50% | p < 0.01 |
| Treated (Ex. 1) | 0% | 0% | |
| Control (Ex. 2) | 40% | 30% | p < 0.03 |
| Treated (Ex. 2) | 0% | 0% | |
| Control (Total) | 50% | 28.6% | p < 0.01 |
| Treated (Total) | 0% | 0% | |

It is to be understood that, while various embodiments of the invention has been described in conjunction with the detailed description thereof, the foregoing is only intended to illustrate and not to limit the scope of the invention, which is defined by the scope of the appended claims. Other related embodiments, aspects, advantages, and/or modifications are within the scope of the following claims.

What is claimed is:

1. A method for treating tissue to reduce post-surgical adhesions, comprising:
   applying energy at a surgical site in a controlled manner;
   measuring at least one treatment completion parameter at said site, said parameter indicative of an amount of energy applied to said surgical site; and
   terminating said applying when said treatment completion parameter reaches a value corresponding to a reduction in said post-surgical adhesions.

2. The method according to claim 1, wherein said energy is applied at a level sufficient to inhibit release of adhesion-inducing substances, but less than sufficient to damage tissue at said surgical site.

3. The method according to claim 2, wherein said energy applied is between about 45 to 125 joules.

4. The method according to claim 3, wherein said energy applied is between about 60 to 75 joules.

5. The method according to claim 3, wherein said terminating occurs prior to a greater than 100% increase in treated tissue impedance.

6. The method according to claim 3, wherein said treatment completion parameter comprises tissue temperature at said surgical site.

7. The method according to claim 6, wherein said temperature value corresponding to a reduction in post-surgical adhesions is between about 61° C. and 100° C.

8. The method according to claim 7, wherein said temperature value is between about 70° C. and 80° C.

9. The method according to claim 8, wherein said temperature value is approximately 75° C.

10. The method according to claim 6 wherein said treatment completion parameter further comprises time.

11. The method according to claim 10, comprising terminating said applying when the temperature is between about 65° C. and 90° C. for a time of less than about 60 seconds.

12. The method according to claim 1, further comprising:
    incising and retracting tissue overlying a patient's peritoneum;
    applying said energy to the peritoneum; and
    making an incision through the peritoneum after said terminating.

13. The method according to claim 12, wherein said applying comprises making a small incision in the peritoneum and inserting a treatment element therethrough to contact an inside surface of the peritoneum.

14. The method according to claim 1, wherein said energy is applied on at least one surface of said tissue at said surgical site.

15. The method according to claim 1, further comprising cutting said tissue at said surgical site to form cut edges thereof.

16. The method according to claim 1 wherein said treatment completion parameter is at least one of tissue impedance, duration of energy application, time of treatment elapsed, and a combination thereof.

17. The method according to claim 1, wherein the energy is heat.

18. The method according to claim 1, wherein the energy is RF energy.

19. A method for treating tissue to reduce post-surgical adhesions, comprising:

applying energy at a surgical site to heat the tissue in a controlled manner without ablating or cauterizing tissue;

measuring the temperature and monitoring the time of heat application at said surgical site; and terminating said applying when temperature has been maintained at between about 61° C. and 100° C. for less than about 60 seconds to reduce post-surgical adhesions from incisions to be made at said surgical site.

20. The method according to claim 19, wherein said applying comprises delivering between about 45 and 125 joules of energy to the tissue.

21. The method according to claim 20, wherein said energy delivered is between about 60 and 75 joules.

22. The method according to claim 20, wherein said temperature is maintained at between about 70° C. and 80° C.

23. The method according to claim 22, wherein said temperature is maintained at about 75° C. for about 5 to 15 seconds.

24. The method according to claim 19, wherein in said energy is applied by a resistive heating element.

25. The method according to claim 19, wherein said energy is applied by RF electrodes.

26. A system for reducing incidence of post-surgical adhesions at surgical sites, comprising:

an applicator member;

at least one treatment element disposed on said applicator member;

a sensor disposed on said applicator member adjacent said at least one treatment element; and a control unit communicating with said sensor and treatment element, wherein the control unit controls the treatment element in response to signals from the sensor to deliver energy to tissue contacted by the treatment element in a controlled manner to reduce the occurrence of post-surgical adhesions due to subsequent incisions at said surgical sites, wherein said applicator member comprises:

an elongate member; and a plurality of expandable flanges positioned at one end of said member, wherein a treatment element is disposed on each of said expandable flanges.

27. The system according to claim 26, wherein said elongate member is a trocar cannula.

28. A method of training a person to treat tissue to reduce incidence of post-surgical adhesions that comprises demonstrating or instructing the performance of the following steps:

applying energy at a surgical site in a controlled manner;

measuring at least one treatment completion parameter at said site, said parameter indicative of an amount of energy applied to said surgical site; and terminating said applying when said treatment completion parameter reaches a value corresponding to a reduction in said post-surgical adhesions.

29. The method according to claim 28, wherein said demonstrating or instructing applying energy step comprises demonstrating or instructing energy application at a level sufficient to inhibit release of adhesion-inducing substances, but less than sufficient to damage tissue at said surgical site.

30. The method according to claim 29, wherein said demonstrating or instructing applying energy step comprises demonstrating or instructing energy application between about 45 and 125 joules.

31. The method according to claim 30, wherein said demonstrating or instructing applying energy step comprises demonstrating or instructing energy application between about 60 and 75 joules.

32. The method according to claim 30, wherein said demonstrating or instructing terminating step comprises demonstrating or instructing terminating prior to a greater than 100% increase in treated tissue impedance.

33. The method according to claim 30, wherein said demonstrating or instructing terminating step comprises demonstrating or instructing that a treatment completion parameter comprises tissue temperature at said surgical site.

34. The method according to claim 33, further comprising demonstrating or instructing that said temperature value corresponding to a reduction in post-surgical adhesions is between about 61° C. and 100° C.

35. The method according to claim 34, further comprising demonstrating or instructing that said temperature value is between about 70° C. and 80° C.

36. The method according to claim 35, further comprising demonstrating or instructing that said temperature value is approximately 75° C.

37. The method according to claim 33, further comprising demonstrating or instructing that said treatment completion parameter further comprises time.

38. The method according to claim 37, wherein said demonstrating or instructing terminating step comprises demonstrating or instructing terminating said applying when the temperature is between about 65° C. and 90° C. for a time of less than about 60 seconds.

39. The method according to claim 28, further comprising instructing or demonstrating the following additional steps:

incising and retracting tissue overlying a patient's peritoneum;

applying said energy to the peritoneum; and making an incision through the peritoneum after said terminating.

40. The method according to claim 39, wherein said demonstrating or instructing applying energy step comprises demonstrating or instructing making a small incision in the peritoneum and inserting a treatment element therethrough to contact an inside surface of the peritoneum.

41. The method according to claim 28, further comprising demonstrating or instructing that said energy is applied on at least one surface of said tissue at said surgical site.

42. The method according to claim 28, further comprising demonstrating or instructing the additional step of cutting said tissue at said surgical site to form cut edges thereof.

43. The method according to claim 28, further comprising demonstrating or instructing that said treatment completion parameter is at least one of tissue impedance, duration of energy application, time of treatment elapsed, and a combination thereof.

44. The method according to claim 28, further comprising demonstrating or instructing that the energy is heat.

45. The method according to claim 28, further comprising demonstrating or instructing that the energy is RF energy.

* * * * *